United States Patent [19]

Evans

[11] Patent Number: 5,194,593
[45] Date of Patent: Mar. 16, 1993

[54] ANTIBODIES TO NATURAL KILLER CELL AND NON-SPECIFIC CYTOTOXIC CELL RECEPTOR AND TARGET CELL ANTIGENS

[75] Inventor: Donald L. Evans, Athens, Ga.

[73] Assignee: University of Georgia Research Foundation, Inc., Athens, Ga.

[21] Appl. No.: 592,685

[22] Filed: Oct. 3, 1990

Related U.S. Application Data

[62] Division of Ser. No. 109,730, Oct. 16, 1987.

[51] Int. Cl.$^5$ .................... C07K 15/28; A61K 39/395
[52] U.S. Cl. ..................... 530/388.73; 530/389.1; 530/387.1
[58] Field of Search ............... 530/387, 387.1, 388.73, 530/389.1

[56] References Cited

U.S. PATENT DOCUMENTS 5,028,424  7/1991  Evans ................................ 424/85.8

OTHER PUBLICATIONS

Jaso-Friedmann et al., J. Immunol. 141, 2861-2868 (1988).
Harris et al., J. Immunol. 143, 727-735 (1989).

*Primary Examiner*—Christine M. Nucker
*Assistant Examiner*—M. P. Woodward
*Attorney, Agent, or Firm*—Kilpatrick & Cody

[57] ABSTRACT

The present invention encompasses a receptor molecule present on the surface of natural killer cells (NK cells) and non-specific cytotoxic cells (NCC) which is involved in non-specific lysis of target cells bearing an antigen recognized by the receptor molecule, an antigen common to the surface of cells recognized and lysed by natural killer cells, monoclonal and heterologous antibodies which bind to the receptor and target cell antigen(s) which are useful in their identification and purification, and methods for altering NK cell-mediated lysis of target cells.

The monoclonal antibodies (mAbs) of the present invention were prepared by cell fusions between spleen cells from mice immunized with either non-specific cytotoxic cells (NCC) from catfish (anti-receptor antibodies) or NC-37 human lymphoblastoid B-cells, which are susceptible to lysis by NK cells, and myeloma cells. Eight distinct mAbs have been characterized, four directed against the NK/NCC target cell receptor and four against the NK/NC cell antigen. As used in the present invention "NK cells" will be used to include both natural killer cells of mammalian origin and non-specific cytotoxic cells of fish origin, unless specifically stated otherwise. Two of the mAbs directed against the receptor and two of the mAbs against the NK target cell antigen are able to significantly inhibit NK lysis at low mAb concentrations, as assessed by inhibition of cellular toxicity. Two of the mAbs directed against the receptor and two of the mAbs against the NK target cell antigen bind to the antigen(s) but do not inhibit lysis.

14 Claims, 2 Drawing Sheets ated killer (LAK) cells
ANTIBODIES TO NATURAL KILLER CELL AND NON-SPECIFIC CYTOTOXIC CELL RECEPTOR AND TARGET CELL ANTIGENS The U.S. government has certain rights in this invention by virtue of grants from the U.S. Department of Agriculture.

This application is a divisional of U.S. Ser. No. 07/109,730 "Antibodies to Receptor and Antigen for Natural Killer and Non-Specific Cytotoxic Cells" filed Oct. 16, 1987, by Donald L. Evans.

This invention is generally in the area of immunology and protein characterization and specifically in the area of protein receptors on natural killer cells.

BACKGROUND OF THE INVENTION

By the early 1970's, natural killer (NK) cell activity, distinct from antigen specific cytolytic T lymphocyte activity, had been reported by several laboratories in a variety of species, including mouse, rat and man. These reports are reviewed by R. K. Oldham, *J. Biol. Resp. Mod.* 1,217 (1982). Non-specific cytotoxic cells (NCC), similar in many aspects to NK cells, also have been identified in lower vertebrate species (Graves et al, *Dev. Comp. Immunol.* 8,293 (1984); Evans et al, *Dev. Comp. Immunol.* 8,303 (1984); Evans et al, *Dev. Comp. Immuno.* 8,599 (1984) Evans et al, *Dev. Comp. Immunol.* 8,823 (1984).

NK cells are known to be a heterogeneous population of immune cells with reagrd to phenotype and function, as discussed, for example, by Lanier et al, *Immunol. Today*, 7,132 (1986). However, controversy still exists with regard to their lineage with respect to other immune cells and to their relationship to other effector cells such as lymphokine-activated killer (LAK) cells and anomolous killer (AK) cells. These differences may reflect the innate heterogeneity of the types of cells capable of NK activity (as defined by function) or be due to the various assay systems employed to study NK cells.

NK cells have been implicated in a variety of activities involving the immune system, including immune disorders in both animal models and man. Results from animal models have also shown that NK cells are effective in vivo against the growth and metastasis of certain types of tumors. In this regard, administration of in vitro cultured NK cells to human cancer patients has shown promise in the treatment and regression of certain types of malignancies. Further, NK cells have been implicated in host resistance to infections with microorganisms, both bacteria and viruses. Finally, NK cells are thought to play an important role in the normal regulation of the host immune system through immunoglobulin production and hematopoiesis. These lines of evidence suggest that the NK system possesses considerable functional diversity, and may operate by the recognition of changes in normal membrane structures, including differentiation antigens, as discussed by Toshitani et al, *Cell Immunol.* 108,188 (1987); Kornbluth et al, *J. Immunol.* 134,728 (1985); Lauzon and Roder, *Cell Immunol.* 94,85 (1985); Roder et al, *J. Exp. Med.* 150,471 (1979).

Although NK cells have been studied for several decades, two of the major questions that remain in NK biology today are what molecule(s) on the surface of NK cells is involved in recognition of the target cells and what molecule(s) on the target cells is recognized by NK cells. At the beginning of the last decade it was found that T cells recognize products of the major histocompatability complex (MHC) expressed on target cells. This discovery was facilitated by the availability of monoclonal antibodies (mAbs) against these molecules which inhibited their recognition by T cells. In terms of NK biology, mAb inhibition of function or recognition (in the absence of complement) has been much less frequently documented. Both the transferring receptor and the receptor for IgG Fc have been implicated to serve as recognition structures for NK cells, although these results are controversial (Vodinelich et al, *Proc. Natl. Acad. Sci. USA* 80,835 (1983); Dokhelar et al, *Eur. J. Immunol.* 14,340 (1984). The laminin/laminin receptor complex has also recently been implicated to act as a means of NK recognition of certain cells, as reported at the Fourth Int'l Workshop on NK Cells, Kingston, Ontario, 1986. Finally, carbohydrate/carbohydrate interactions have been implicated to serve as a means of NK/target cell recognition by Muchmore et al, *Immunolbiol.* 158,191 (1981); Werkmeister et al, *Cell. Immunol.* 80,172 (1983). Together, these results have been interpreted as signifying that NK cells do not express clonally-restricted receptors, that NK cells may express more than one receptor on their surface and that NK cells are capable of recognizing multiple antigens on the surface of one or more target cells. These results may also be indicative of NK heterogeneity due to discrete NK subpopulations.

The NK cell membrane antigens and mAbs capable of detecting these determinants are shown in Table I.

TABLE I

| Natural Killer cell membranes antigens and mAbs capable of detecting these determinants. | |
|---|---|
| mAb Designation | Antigen Specificity |
| CD2 (Leu-5b) | T cells, NK cells |
| CD7 (Leu-9) | T cells, NK cells |
| CD8 (Leu-2) | T cells, NK cells |
| CD11 (Leu-15) | C3bi receptor on T cells, NK cells, monoctyes and macrophages |
| CD16 (Leu-11a) | Fc (gamma) receptor on NK cells and on PMN's |
| Leu 7 | HNK-1 on LGL's and NK cells |
| Leu 19 | NKH-1 determinant (220 KD) on NK and T-cells |
| a)OKT8 | T cytotoxic/suppressor cells and LGL |
| OKT10 | LGL, early thymus antigen |
| 3A1 | T cells and LGL |
| 5A12 | T cells and LGL |
| Lyt 3 | T cells and LGL |
| OKT5 | T cytotoxic/suppressor cells and LGL |
| Ia | Activated T cells | a)Cells expressing OKT8, OKT5 and Ia are nonlytic LGL's.

Although typical NK activity is generally accepted to be mediated by cells with the Leu4− (CD3−), Leu11+ (CD16+) and Leu 19+ surface phenotype, there is compelling evidence that typical T cells, particularly antigen-specific cytotoxic T cells (CTL), can mediate NK-like cytotoxicity as measured against certain tumor cells such as K562, as described by Brooks et al., *Immunol. Rev.* 72, 43 (1983) and others. These CTLs are referred to as CTL(NK) or non-MHC-restricted CTL. Since it has been shown that true NK cells do not transcribe mRNA for or express on their surface a typical T cell antigen receptor (TCR) (Reynolds et al, *J. Exp. Med.* 150,471 (1985); Lanier et al, *J. Exp. Med.* 163,209 (1986); Tutt et al, *J. Immunol.* 137,2998 (1986)), it is generally accepted that NK cells do not recognize antigen in this fashion and do not recognize MHC molecules. Although the CTL(NK) do express a typical TCR, it is not known whether this molecule is utilized to effect their NK-like killing or if these effector cells recognize MHC antigens in some aberrant fashion. Recently, there has been evidence to suggest that the CD3 molecule and the gamma/delta TCR may be involved in this type of non-MHC-restricted cytotoxicity (Farrini et al, *J. Exp. Med.* 166,277 (1987); Alarcon et al, *Proc. Natl. Acad. Sci.* USA 84,3861 (1987); Ang et al, *J. Exp. Med.* 165,1453 (1987); David et al, *J. Immunol.* 138,2831 (1987); van de Grien et al, *J. Immunol.* 138,1627 (1987). In other studies, it has been demonstrated that anti-CD3 and anti-CD8 mAb's, while inhibiting the antigen-specific lysis by such CTL clones, do not inhibit the NK-like lysis by these effector cells (Moretta et al, *Eur. J. Immunol.* 14,121 (1984); Brooks and Holscher, *J. Immunol.* 6,594 (1987); Roberts and Moore, *Eur. J. Immunol.* 15,448 (1985).

Very little is known regarding identification of lymphoreticular cells in fish. Previous studies have tentatively identified a B lymphocyte subpopulation in this species. However, there have been only a few investigations where attempts have been made to identify cytotoxic cells in teleost fish. In mammals, however, a great deal is known regarding the heterogeneity of lymphocytes and mAbs have been derived which inhibit cytotoxic activity. For example, anti-OKT3 mAbs identify a determinant found on most human T cells. Monoclonal antibodies specific for this antigen inhibit CTL killing of Epstein-Barr virus infected cells. The OKT10 determinant is present on human natural killer cells as well as on other cells and anti-OKT10 mAbs inhibit NK lysis of K652, MOLT-4, and CEM tumor targets. Monoclonal antibodies directed against the glycoprotein T-200, an antigen that is present on all human peripheral blood T-lymphocytes, blocks the ability of K562 cells to inhibit NK killing of MOLT-4 cells in cold target inhibition assays. The mAb NK-8 inhibits LGL mediated cytotoxicity against K562 cells by 50 to 60%. Two mAbs (RH 7.2 and 17.2) directed against alloimmune human cytotoxic lymphocytes inhibit NK cytolysis when added at the $Ca^{++}$ pulse phase.

It therefore seems apparent that in order to understand the process of NK cell recognition, it is essential to identify and characterize examples of NK target antigens, as well as the receptor(s), in a variety of species, including lower vertebrates such as fish and mammals.

Knowledge of an NK antigen receptor would enable analysis of how the receptor/ligand complex functions. Further, isolation of an NK antigen receptor would allow comparison with other receptors and possibly the identification of other NK antigen receptors or subclasses of NK cells on the basis of antigen specificity and/or type of antigen receptor. This would further understanding of the relationship between NK, LAK and CTL(NK) populations as well as immune cells such as monocytes, macrophages and other types of T cells. A comparison of the receptor molecules in fish, mouse and humans provides insights into the evolution of the NK cell population and the role they play in immune function, malignancy and immune disorders.

Knowledge of NK target antigens allows comparisons with other known ligands recognized by effector cells, such as MHC molecules, and could lead to the identification of other target antigens that may be similar in normal host defense, tumor biology and NK cell regulation. Further, as true for the NK cell receptor, identification of an NK target antigen could serve to classify NK cells into discrete subpopulations based on "antigen specificity", in that there may be subpopulations of NK cells which preferentially recognize certain target antigens. Knowledge of these molecules may have important implications concerning the types of antigen receptors present on other types of nonspecific effector cells. An analysis of the target antigen at the biochemical level may lead to a better understanding of what types of molecules are important in NK cell recognition and the role of these cells in the immune system. A comparison of the target antigens in fish, mouse and man at the biological, biochemical and molecular levels should give some insight into the evolution of the NK population in the immune system and possibly as to what challenges to the immune system this system evolved to combat. That is, if these target antigens are very conserved, at all levels of analysis, this may indicate the existence of important regulatory structures in the host and thus strong evolutionary pressures on the NK system to maintain a method by which to recognize these molecules. The anti-target cell mAb's may be of in vivo relevance in that, if NK cells are important in defense against malignancy, then an understanding of the recognition and regulation of this antigen may be useful in the detection and treatment of cancer via screening for malignancy and immune disorders, and for targeting of NK cells or mAbs to tumors.

It is therefore an object of the present invention to provide antibodies which specifically recognize and bind to antigens on the surface of NK cells and cells lysed by NK cells.

It is a further object of the present invention to provide such antibodies which can inhibit the lysis of target cells by NK cells.

It is a still further object of the present invention to provide antibodies which are useful in the isolation and characterization of NK cell populations as defined by their antigen receptors and molecules recognized thereby, as well as the actual antigens.

SUMMARY OF THE INVENTION

The present invention encompasses a receptor molecule (dimer) present on the surface of natural killer cells (NK cells) and non-specific cytotoxic cells (NCC) which is involved in non-specific lysis of target cells bearing an antigen recognized by the receptor, an antigen common to the surface of cells recognized and lysed by natural killer cells, monoclonal and heterologous antibodies which bind to the receptor and antigen molecule(s) which are useful in their identification and purification, and methods for altering NK cell-mediated lysis of target cells.

The monoclonal antibodies (mAbs) of the present invention were prepared by cell fusions between spleen cells from mice immunized with either non-specific cytotoxic cells (NCC) from catfish (anti-receptor antibodies) or NC-37 human lymphoblastoid B-cells, which are susceptible to lysis by NK cells, and myeloma cells. Eight distinct mAbs have been characterized, four directed against the NK/NCC cell receptor and four against the NK/NCC recognized target cell antigen. As used in the present invention "NK cells" will be used to include both natural killer cells of mammalian origin and non-specific cytotoxic cells of fish origin, unless specifically stated otherwise. Two of the mAbs directed against the receptor and two of the mAbs against the NK cell antigen are able to significantly inhibit NK lysis at low mAb concentrations, as assessed by inhibition of cell-mediated cytotoxicity assays. Two of the mAbs directed against the receptor and two of the mAbs against the NK cell antigen bind to the protein(s) but do not inhibit lysis.

DETAILED DESCRIPTION OF THE INVENTION

Figure 1:
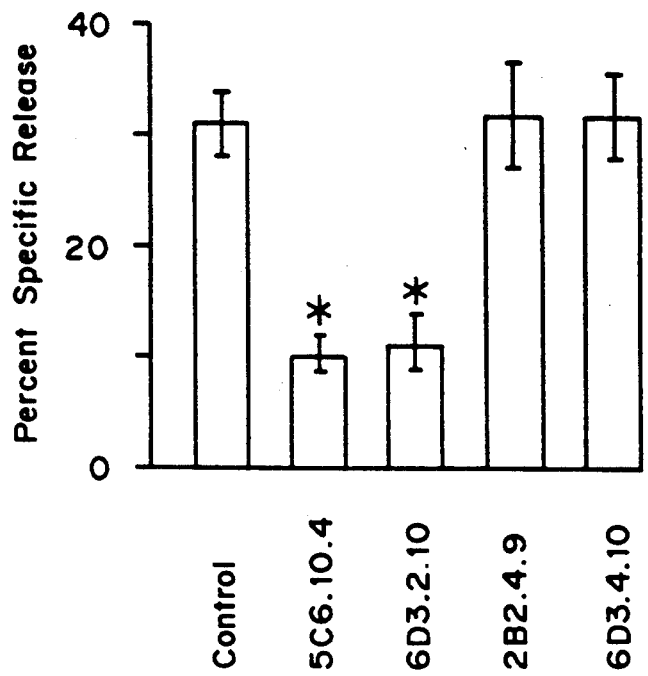
FIG. 1 compares the inhibitory effect of mAbs 5C6.10.4 and 6D3.2.10, as well as mAbs 2B2.4.9 and 6D3.4.10 of $^{51}$Cr-labeled NC-37 target cells. Effector cells were incubated with 10 μg of mAb for 4 h, washed 2×, and mixed with target cells at an effector to target cell ratio of 160:1.

The present invention is a receptor protein found on the surface of natural killer cells and non-specific cytotoxic cells (jointly referred to hereafter as "NK cells" unless stated otherwise) in a variety of species, including man, mouse, rat, and fish, a protein recognized by the receptor when present on the surface of eucaryotic cells, which results in lysis of the protein bearing cells, and monoclonal and heterologous antibodies to both the protein receptor and target protein. The present invention also includes methods for their isolation, characterization and use under a variety of conditions.

Non-specific cytotoxic cells (NCC) represent a population of cells that mediate "natural" cellular immunity in the catfish (*I. punctatus*), analogous to mammalian natural killer (NK) cells. NCC bind to and lyse a variety of transformed murine and human B-cell, T-cell and myeloid targets. Similar to NK cells, NCC require cell-cell contact for initiation of the first stage of lysis; NCC are plastic and nylon wool nonadherent; NCC require a period of preincubation prior to addition of target cells to augment killing; and, like NK cells, NCC have similar $Mg^{++}$ and $Ca^{++}$ requirements for binding and killing, respectively.

Additional comparisons have been made between NCC and NK cells using Michaelis-Menten Kinetics and Lineweaver-Burk transformation studies. Approximately five times more NCC cells are required to kill an individual target cell compared to NK cells and, in a three hour killing assay, NCC do not recycle. However, NCC may be more pluripotent and functionally undifferentiated when compared to mammalian NK cells, as shown by comparisons demonstrating rapid killing kinetics, extremely wide temperature optima and multiple target cell phenotype specificities. NCC produce rapid lysis of target cells (90% of total lysis within 90 minutes) and NCC bind to and lyse a wide variety of different types of target cells. These targets included YAC-1, P815, NC-37, DAUDI, P3HR-1, MOLT-4, K562, U937, and HL-60 cells.

This very large spectrum of target cell killing indicates either that recognition is entirely antigen nonspecific or that two different determinants are required for NCC recognition and lysis of a target. Cold target inhibition has shown that NCC are comprised of many different subpopulations of antigen specific cells and that homologous, but not heterologous cold targets, inhibit lysis. In addition, cells which have similar properties, such as certain Epstein-Barr transformed B-cells (NC-37, P3HR-1, DAUDI) which are susceptible to lysis, can reciprocally act as cold targets to inhibit lysis by NCC. These data suggested that multiple different target cells could be recognized by different subsets of NCC, and that clonotypic-like NCC functions could be mediated by a specific antigen receptor(s).

Target Cell Antigen

Isolation of mAbs Directed Against a Target Cell Antigen

Since NCC lysis is characterized as being non-MHC-restricted and NCC are capable of lysing a variety of transformed human cell lines, including NC-37 (a human lymphoblastoid B-cell line), DAUDI (a human lymphoblastic B cell line) and P3HR-1 (Same as DAUDI), and the naturally occurring fish parasite *Tetrahymena pyriformis* as well as several murine cell lines such as YAC-1 (a mouse lymphoma induced by Moloney Leukemia virus), and because the parasite targets will cold-compete with the tumor cell lines in cytotoxicity assays, it appeared that certain human and murine transformed cell lines shared some common antigenic determinant with a fish parasite that is recognized by fish NCC. For this reason, the NC-37 cell line was used as a source of antigen in the generation of mAbs.

Spleen cells from NC-37 primed Balb/c mice were fused with P3-X63-Ag 8.653 myeloma cells. The resulting mAbs were screened with *Tetrahymena pyriformis* and the NC-37 cell line for those mAbs which reacted with both in an ELISA. Four independent positive binding mAbs then were chosen for expansion and cloning by repeated limiting dilution. These mAbs are designated 1E7, 18C2.8.3, 1D4 and 7C6.5.4. 18C2.8.3, which produces IgM mAbs that bind to target antigen and inhibit NK-mediated lysis, and 7C6.5.4, which produces IgG mAbs that bind to target antigen but do not inhibit NK-mediated lysis, were deposited with the American Type Culture Collection, Rockville, MD, on Oct. 16, 1987 and designated ATCC numbers HB9571 and HB9574, respectively. All of the mAbs were grown in ascites and purified from the ascites by Sepharose-Protein A (IgG) or Sepharose-Con A (IgM) chromatography prior to testing.

Characterization of mAbs Against A Target Cell Antigen

The following studies show that monoclonal antibodies derived against NC-37 cells specifically inhibit fish NCC lysis of target cells. Inhibition of cytotoxicity by mAbs 18C2.8.3 and 1E7 is dose dependent with inhibition located at the target cell level. All of the target cell lines studied, whether of human or of mouse origin, are protected from NCC lysis by prior treatment with these mAbs. Other mAbs (7C6.5.4 and 1D4) bind to the target cells but do not inhibit lysis. These data indicate that the determinants recognized by mAbs 18C2.8.3 and 1E7 are the same (or at least part of the same antigenic complex)

and that inhibition of lysis is probably not the result of steric hindrance.

The specificity of the mAbs was studied by adsorption experiments. It was demonstrated that if the mAbs were previously adsorbed with a variety of different target cell lines, then the ability of the mAbs to inhibit lysis of NC-37 target cells by NCC was lost. This response demonstrated that the antigenic determinants recognized by the mAbs were the same on the adsorbing cells as those found on the NC-37 target cells and that the antigenic determinants were present on the cell surface membrane.

The widespread cellular distribution of these mAbs-defined antigenic determinants was further shown by experiments demonstrating inhibition of lysis of *Tetrahymena pyriformis* by mAb 1E7. In addition, adsorption of the inhibitory mAb with different numbers of the parasite selectively removed the inhibitory activity of the mAb when tested in a lytic assay against NC-37 target cells. This result demonstrated that the mAb recognized the same antigenic determinant(s) on both mammalian and protozoan target cells.

Mechanism of Inhibition of mAbs Directed Against a Target Cell Antigen

Flow cytometry analysis of the cell lines with FITC-labeled mAb showed the highest levels of binding for both inhibitor mAbs and of noninhibitor mAb 1D4, and low levels of mAb 7C6.5.4 binding. These results are in agreement with the data obtained with the NC-37 coated ELISA plates. Although mAbs 18C2.8.3, 1E7, 7C6.5.4, and 1D4 showed varying levels of binding to the cell lines, all four mAbs bound to some degree to the target cells tested.

Inhibition of NCC Cytotoxicity by mAbs Directed Against a Target Cell Antigen Each target cell-NCC mixture was incubated with different dilutions of each purified mAb in a standard $^{51}$Cr-release assay. Four mAbs were tested for their ability to inhibit the lysis of a battery of target cells by NCC, including NC-37 (this cell line carries EBV genomic sequences but EBV membrane antigens are not expressed), DAUDI, MOLT-4 (human leukemic T-cell), HL-60 (human promyelocytic leukemic cell), K562 (human erythromyeloid leukemia), U937 (human histiocytic leukemia), P815 (mouse mastocytoma) and YAC-1. Purified mAbs 18C2.8.3 and 1E7 (IgM isotype) inhibited NCC killing of the following targets: U937, MOLT-4, K562, HL-60, DAUDI, NC-37, P815, and YAC-1. The dose dependent inhibitory activity ranged from 50 to 70% at a concentration of 50 μg/well when compared to non-inhibitory mAbs 7C6.5.4 and 1D4 (IgG isotype). Similarly, mAb 18C2.8.3 protected the fish parasite *Tetrahymena pyriformis* from lysis by NCC when compared to mAb 7C6.5.4. Adsorption studies demonstrated that the inhibitory effect on NC-37 lysis by NCC could be removed in a titratable fashion by incubation of mAb 1E7 with any one of the other target cell lines. The inhibitory activity of mAbs 1E7 and 18C2.8.3 was shown to be due to the inhibition of conjugate formation between effector (NK/NCC) and NC-37 target cells.

The mAbs 1E7 and 18C2.8.3 inhibit NCC lysis in a dose-dependent manner while the mAbs 1D4 and 7C6.5.4 are not inhibitory for cytotoxicity. An irrelevant mAb (referred to as 6D3H.10) of the same IgM isotype as the inhibitory mAbs also had no effect on cytotoxicity. Similarly, when *Tetrahymena pyriformis* was used as the labeled target cell, mAb 18C2.8.3 (but not mAb 7C6.5.4) blocked approximately 70% of the killing by NCC. Inhibition is specific for the target cell as preincubation of the targets followed by washing still results in inhibition of lysis. Further, incubation of the NCC effector cells with the mAbs, followed by washing, does not result in inhibition of lysis. These data indicate that the determinants recognized by mAbs 1E7 and 18C2.8.3 are identical to, or are in close proximity to, those antigenic determinants recognized by the fish NCC effector cells. Inhibition does not seem to be due to effects of steric hinderance as both non-inhibitory mAbs (1D4 and 7C6.5.4) bind to the target cells.

The widespread phylogenetic distribution of these antigenic determinants was further demonstrated by the inhibition of the lysis of the parasite Tetrahymena by NCC with the mAb 18C2.8.3 but not 7C6.5.4.

The relative levels of these mAb-defined determinants on the target cells was measured with fluorescent flow cytometric analysis (FCM) using FITC-labeled mAbs. These experiments showed that all four mAbs bound to the surface of the cells tested. Biochemical analysis with Western blots and immunoprecipitation showed that mAbs 18C2.8.3 and 1E7 recognize two antigens in NC-37 lysates: a larger protein of around 80,000 D and a smaller one of 42,000 D. The antigen(s) recognized by mAb 1E7 is expressed at the highest levels on all of the target cells. Further, concentrations of these determinants on the target cells seemed to parallel their sensitivity to lysis, i.e., NC37 cells (most sensitive to lysis) express very high levels of this antigen while P815 cells (less sensitive to lysis) exhibit low concentrations of this determinant.

Due to the widespread phylogenetic distribution of the target cell molecule, the effect of the mAbs on the NK activity of another unrelated species, baboon, was examined. Peripheral blood was collected and lymphocytes purified by density separation. The mAb 18C2.8.3 was tested for its ability to inhibit NK lysis by these effector cells. Four of six animals exhibited NK activity that was inhibited by this mAb in a dose-dependent fashion, confirming that this mAb recognizes an antigenic determinant recognized by baboon NK cells from a majority of such animals.

Several human cell lines routinely used to test for human NK activity were also examined for the expression of the molecules defined by the mAbs 1E7, 18C2.8.3 and 7C6.5.4. This determinant was expressed on K562, NC37, Molt 4, Daudi and SB cells. Interestingly, this antigen was present at the highest levels on those cell lines that were the most sensitive to NK lysis (K562, NC37 and MOLT 4). When the mAbs were tested in a 3 h cytotoxicity assay, both the 1E7 and 18C2.8.3 mAbs were found to significantly inhibit, in a dose-dependent manner, the NK lysis of four different target cells. As observed in the fish NCC system, although the mAbs 1D4 and 7C6.5.4 bound to the target cells, they did not inhibit human NK lysis of the target cells.

The ability of these mAbs to inhibit the NK lysis of other human effector cell populations was also examined. The mAbs were observed to be capable of inhibiting the lytic activity of both activated NK cells (24 h incubation with IL 2) and 5 d lymphokine-activated killer (LAK) cells. It should be noted that higher concentrations of the mAbs were required to achieve maximal inhibition of these effector cell populations than observed with fresh NK cells, possibly indicative of effector cells with a higher affinity for the target cells. These results indicate that fresh NK cells, activated NK cells and LAK effector cells do, at least in part, recognize the same antigenic determinant on certain target cells.

Finally, these mAbs were tested for the ability to inhibit the NK-like lysis of antigen-specific CTL. It was observed that the mAbs 1E7 and 18C2.8.3 had no effect on the antigen-specific lysis exhibited by these CTL, although the W6/32 mAb (anti-HLA) was effective in this regard. However, these mAbs were very effective in inhibiting the lysis of K562 target cells by these CTL while the W6/32 mAb was ineffective.

These results imply that antigen-specific CTL are capable of recognizing a determinant on certain target cells distinct from MHC molecules, and which appears to be identical to those determinants recognized by conventional NK cells. This finding may imply that such CTL possess more than one antigen receptor on their surface, one for specific antigen (MHC recognition mediated by a typical TCR) and one for NK antigen determinants (recognition of the antigen defined by the present mAbs and mediated through receptor "X"), which are independent from each other. It should be noted that the level of inhibition of lysis varied from individual to individual, which may be indicative of the existence of different NK subpopulations which recognize this determinant in different individuals. These results are also indicative of the existence of other target antigens on these tumor cell lines.

Target Cell Adsorption Studies

To further investigate the expression of the mAb-defined determinant(s) on different target cells, adsorption experiments were performed. Each mAb was adsorbed with three different concentrations of the indicated target cell. The adsorbed mAbs were then added to $^{51}$Cr-labeled NC-37 target cells and incubated with fish NCC in a 4 h lytic assay. A dose-dependent inhibitory response was observed demonstrating that the antigenic determinant recognized by the mAb was the same on the adsorbing cell as on the labeled NC-37 target cells. Adsorption of mAb 1E7 with Tetrahymena demonstrated that the same determinant recognized by NCC is present on the surface of this protozoan as well as on NC-37 cells.

Target cells were next treated with each mAb to determine if inhibition of conjugate formation occurred. NC-37 cells (1.5×10⁶ cells) were treated with 75 or 150 μg of each mAb, washed, and added to fish NCC (1:2 E:T ratio). Significant dose dependent inhibition of conjugate formation was observed in samples pretreated with mAbs 18C2.8.3 and 1E7, when compared to NMS treatment. The noninhibitor mAbs 7C6.5.4 and 1D4 had no significant effect on conjugate formation. Similarly, cytotoxicity experiments conducted with pretreated $^{51}$Cr-labeled target cells indicated that lysis of NC-37 cells was also inhibited by mAbs 18C2.8.3 and 1E7 but not by 7C6.5.4 and 1D4.

Single color flow cytometric analysis was performed in order to determine the relative membrane levels of each of the determinants recognized by mAbs 1E7, 18C2.8.3, 7C6.5.4, and 1D4. Fluorescence histograms of the binding of both inhibitory mAbs 18C2.8.3 and 1E7 to human target cells showed high binding levels to all of the cell lines tested ranging from approximately 40 to 75% of the cells. Similarly, both mAbs (18C2.8.3 and 1E7) bound to approximately 70% of the mouse target cells. Although generally at a lower level than the inhibitory mAbs, different levels of binding were observed for the noninhibitor mAbs 7C6.5.4 and 1D4 among the human and mouse target cells. Binding levels of mAbs 7C6.5.4 and 1D4 ranged between 2 and 10% of the human target cells tested. The highest binding for mAbs 7C6.5.4 and 1D4 was observed with YAC-1 cells (25 and 29%, respectively).

Isolation and Characterization of a Target Cell Antigen

Biochemical analysis of the antigens recognized by the target cell specific mAbs was accomplished by Western blotting and by immunoprecipitation studies. Both techniques revealed that each inhibitory mAb bound to two proteins. Using Western blot analysis, one molecule was of 42,000 D while the second was of 78,000 D or 86,000 D depending on which mAb was used (mAbs 1E7 or 18C2.8.3, respectively). Similar to the Western blot analysis, immunoprecipitates with either mAb 1E7 or 18C2.8.3 revealed a 42,000 D antigen. Unlike Western blot analysis, however, the second and larger molecule precipitated was of 80,000 D. The apparent differences in molecular weight exhibited by the 78, 80, and 86 kD molecules may potentially be due to variation in glycosylation or gel-to-gel variation during SDS-PAGE analysis. It is possible that the larger protein, of approximately 80 kD, may be a dimer of the 42,000 D antigen. Using different reducing conditions (varying beta-mercaptoethanol concentrations and times/temperatures of incubation) did not produce a single band at 42,000 D.

Monoclonal antibody 7C6.5.4 recognized a 67,000 D protein. Although 1D4 did not bind to the nitrocellulose membrane, the flow cytometry data indicate that it binds NC-37 cells. It is possible that the peptide recognized by 1D4 is not solubilized by our procedure. Alternatively, 1D4 may be incapable of binding to its homologous antigen once it is fixed onto nitrocellulose due to a low binding affinity.

The results indicate that the target cell antigen recognized by these mAbs is involved in the recognition process necessary for lysis of target cells by fish NCC and has important implications in the study of host defense, tumor biology, and the recognition process of cytotoxic cells.

Further characterization of the target cell antigen(s) was achieved by separation of the proteins obtained from NC-37 cell lysates via SDS-PAGE and identification by Western blot analysis. mAb 1E7 reacted with two proteins of molecular weights 78,000 and 42,000 D, while mAb 18C2.8.3 recognized a 42,000 D antigen as well as an 86,000 D protein. MAb 7C6.5.4 bound to an antigen with a molecular weight of 64,000 D and 1D4 showed no binding by Western blot analysis. A combination of all four mAbs was incubated with a nitrocellulose strip and the results yielded the sum of the number of bands observed with each individual antibody. No differences were observed when the gels were run under either reducing (5% beta-mercaptoethanol) or non-reducing conditions. Normal mouse serum, used as a negative control, displayed no reactivity.

Determination of the Range and Extent of Target Cell Antigen Distribution $^{35}$S-methionine-labeled NC-37 cell lysates were precipitated with mAbs 18C2.8.3 and 1E7 bound to protein A beads, eluted, and separated by electrophoresis on 11% SDS-PAGE. Two major antigens were eluted from the immune complexes with molecular weights of 42,000 D and 80,000 D, respectively.

These observations are in agreement with the primary molecule observed in the immunoprecipitation experiments with these mAbs and NC37 tumor cells, which appears to be a dimeric complex. Based on the binding data, the mAbs do not appear to recognize Fc gamma receptors, transferrin receptors, laminin receptors or laminin, immunoglobulin, Epstein-Barr viral antigens or MHC antigens. In fact, antibodies directed against MHC molecules, which are very conserved in structure, do not recognize such molecules across such disparate species. Thus, it appears that the mAbs define novel, simple and conserved molecules which serve as NK target antigens in the process of NK lysis. This molecule probably evolved early in the evolution of the immune system to function in regulation of the developing immune system. In fact, this molecule may have some as yet undetermined physiological role.

In order for the target cell molecule to meet the definition of an NK target antigen it must be expressed only on target cells sensitive to NK lysis, or there should be a quantitative difference in the expression of this molecule on sensitive versus insensitive target cells as appears to be the case for this molecule. These conditions need not be met if the target antigen is a polymorphic molecule, as is true for MHC antigens. However, as NK cells do not appear to recognize target cells in the same fashion as T cells, it is unlikely that the NK target antigen is nonpolymorphic. Certain molecules such as MHC antigens are widely distributed throughout the body. Other molecules, such as Thy 1 antigens, are found on limited cell populations such as T cells and brain. Still other molecules have very narrow distribution ranges, such as the CD8 determinant which is found only on certain T cell subpopulations. The expression of these molecules has been useful in defining function and in classifying certain immune disorders. Establishing the distribution of the target cell molecule(s) in mouse and man is therefore useful in terms of defining cells that are recognized and/or regulated by NK cells and in terms of the role of the NK cells in the immune system.

Flow cytometric (FCM) techniques are utilized to determine the range of cells and tissues that express the target cell antigen. Indirect immunofluorescence methods are used for one-color FCM, while two-color FCM is used to simultaneously assess the expression of the target cell antigen and any other antigen of interest. For the two-color analysis, the mAbs are directly conjugated with either FITC or phycoerythrin (PE) using commercially available techniques. An expanded panel of in vitro cultured cell lines including transformed cells of T, B, macrophage and other lineages (for example sarcoid tumors and various embryonic cell lines) and a panel of B cell lines that have been well-characterized as to their levels of various membrane antigens, stage of B cell maturation and sensitivity to NK lysis is then examined for the expression of the molecule to correlate levels of expression of the target cell antigen with susceptibility of these B cell lines to NK lysis. Since the sensitivity of these cell lines to NK lysis has been shown to be influenced by the level of MHC antigens expressed on these cells, these antigens, HLA-A,B,C, can be examined and a determination of the effects of the levels of these two antigens on the sensitivity of the B cells to lysis made. Normal tissue, freshly isolated peripheral blood cells (T, B and macrophages) as well as samples from spleen, thymus and bone marrow and nonhematopoietic tissues, can also be examined for the expression of this molecule.

Although only the ability of the mAbs to inhibit NK lysis has been examined, one of the several functions associated with NK cells, it is possible these mAbs can inhibit activities such as target cell antigen-stimulated proliferation and lymphokine production and augment NK function in the same way that anti-TCR complex mAbs can both augment and inhibit T cell function.

Standard 3h $^{51}$Cr-release microcytotoxicity assays are used to determine the ability of the anti-target cell mAbs to inhibit NK lysis. The assays are performed with and without removal of the mAbs from the assays, varying concentration to determine dose-response of mAb concentrations.

The mechanism of inhibition is determined by analyzing at what stage in the NK lytic process the mAbs act. Since it is assumed that the mAbs define an NK target antigen, conjugate assays are first performed to determine if the mAbs prevent recognition of the target cells. These assays are carried out in suspension by mixing target and purified effector cells (either pretreated with the various mAbs or untreated) together at 23° C. for 15 min and counting conjugates under the light microscope. To determine lytic conjugates, the mixtures are incubated at 37° C. for 30 min, Trypan blue dye added, and viable and dead conjugates enumerated. These relatively simple and expedient conjugate assays are confirmed with the standard conjugate assays in agarose. Any effects at a post-binding phase of the lytic process can also be determined by performing the cytotoxicity assays in a $Mg^{2+}$-containing, $Ca^{2+}$-free buffer with the addition of the mAbs at various times before or after the addition of $Ca^{2+}$.

The ability of the mAbs to inhibit other aspects of NK function can also be determined using short-term antigen-stimulated proliferation assays. NK cells are plated with and without irradiated feeder cells, a stimulus (combinations of IL 2, tumor cells and lectins) and IL 2 in 96 well microtiter plates. Six hour pulses with $^3$H-thymidine added 1–5 days post-initiation are used to show the effects of the mAbs on proliferation. Other antigen-stimulated NK functions which can be examined include the ability of the mAbs to inhibit lymphokine production (for example, IFN-gamma). Lymphokine production assays can be set up as for the proliferation assays except that 24 h after initiation the supernatants are collected and analyzed for IFN-gamma content.

To determine what NK populations are affected by the mAbs, limiting dilution analyses (LDA) are performed to assess the effects of the mAbs on NK proliferation and lymphokine production. The LDAs are set up similar to the above described assays except that graduated numbers of purified NK cells (0.5–100×10$^3$ cells/well) are used. Knowledge of the frequency of NK cells inhibited by these mAbs allows determination if all NK cells are equally affected; if susceptible and nonsusceptible NK populations exist; and if different subpopulations of NK cells exist that recognize different antigens on the target cells.

The activity and biochemistry of the antigen molecules can also be modulated at the surface of the target cells. The modulated target cells can then be tested for their ability to be recognized and lysed by the various NK populations. This can be used to determine whether certain target cells (e.g., K562 cells) express more than one Nk target antigen. Modulations are performed by adding mAbs, followed by the addition of a second anti-mouse Ig antibody, and incubating the cells at 37° C. overnight. The cells are washed and assessed by FCM for the expression of the molecules. FCM can be used to assess whether any other target cell surface molecules are co-modulated via other intermolecular associations.

The ability of mAb-modulated target cells to cold-target inhibit NK lysis is also analyzed, similar to the method described above. First, a correlation of the level of expression of the target cell molecule (via FCM) with the ability of unmodulated target cells to cold-target inhibit NK lysis is made using a panel of NK target cells and NK effector cells. Next, mAb-modulated target cells (modulation assessed by FCM) are analyzed for their ability to cold-target inhibit the lysis of untreated target cells. This determines if more than one target antigen exists on these target cells, and whether NK cells, especially NK clones, recognize more than one NK target antigen.

It is expected that all NK functions which involve antigen recognition, lysis of tumor cells, and antigen-stimulated proliferation and lymphokine production will be inhibited. It is not expected that IL 2-induced proliferation will be affected.

NK CELL RECEPTOR

Isolation and Characterization of mAbs Directed Against NK Cell Receptor mAbs were produced against the NK cell receptor using a similar methodology to that described with respect to the target cell antigen. mAbs were derived against flow cytometry purified fish (*Ictalurus punctatus*) nonspecific cytotoxic cells (NCC). Four mAbs were cloned and characterized. MAbs 5C.10.4 and 6D3.2.10 produce 60-65% inhibition of lysis of NC-37 target cells (a human B-lymphoblastoid cell line) by unfractionated NCC. MAbs 2B2.4.9 and 6D3.4.4 are noninhibitors of cytotoxicity. All mAbs are the same isotype (IgM) and are cloned by limiting dilution (2×). Inhibitory activity is specific for the effector cells because the mAbs have no effect on NCC cytotoxicity when only the target cells are treated. Inhibition can be produced by preincubation of the mAbs with NCC or by no preincubation. Inhibition is not reversible. Approximately 100% inhibition is produced by treatment of flow cytometry (FCM) purified NCC with the inhibitor mAbs. Inhibition of cytolysis was specific for the effector cells and not the target cells since preincubation of the target cells with mAbs 5C6.10.4 (inhibitory mAb) or 6D3.4.4 (noninhibitory mAb) followed by removal of the mAbs prior to the addition of the effector cells did not inhibit lysis. Both inhibitor mAbs significantly inhibit conjugate formation between effector and NC-37 target cells.

Two of the mAb directed against the NK Cell receptor, 5C6.10.4 and 6D3.4.4, were deposited with the American Type Culture Collection on Oct. 16, 1987 and designated HB9572 and HB9573, respectively.

Flow cytometry is also used to determine mAb binding to various effector cell populations. Inhibitor and noninhibitor mAbs bind to approximately 25% (5C6.10.4) and 39% (6D3.4.4) of fish anterior kidney cells; to 42% (5C6.10.4) and 54% (6D3.4.4) of fish spleen cells; and to 2.5% (5C6.10.4 and 6D3.4.4) of fish peripheral blood.

Optimization of Inhibition of NCC Lysis by mAbs Directed Against the NK Cell Receptor To determine the requirements needed to produce optimal inhibition of NCC lysis, each mAb was first purified using Con A Sepharose. The mAbs were next either preincubated with the effector cells for 4 hours (and washed 2×) or not preincubated but added at the start of the cytotoxicity assay. Both incubation protocols were equally efficient in inhibiting NCC lysis, producing 74% (5C6) and 68% (6D3.2) inhibition. See FIG. 1. FIG. 1 shows inhibition of NCC activity by inhibitor mAbs 5C6.10.4 and 6D3.2.10. MAbs were first purified using Con-A sepharose and 10 micrograms was added to each effector: target cell mixture (160:1 E:T ratio). Values are mean ± SD of three replicates. Asterisks indicate values significantly different from controls (P=0.005). Inhibition by the mAbs was not reversible. Extensive washing of the mAb treated effector cells did not remove any inhibitory activity.

Figure 2:
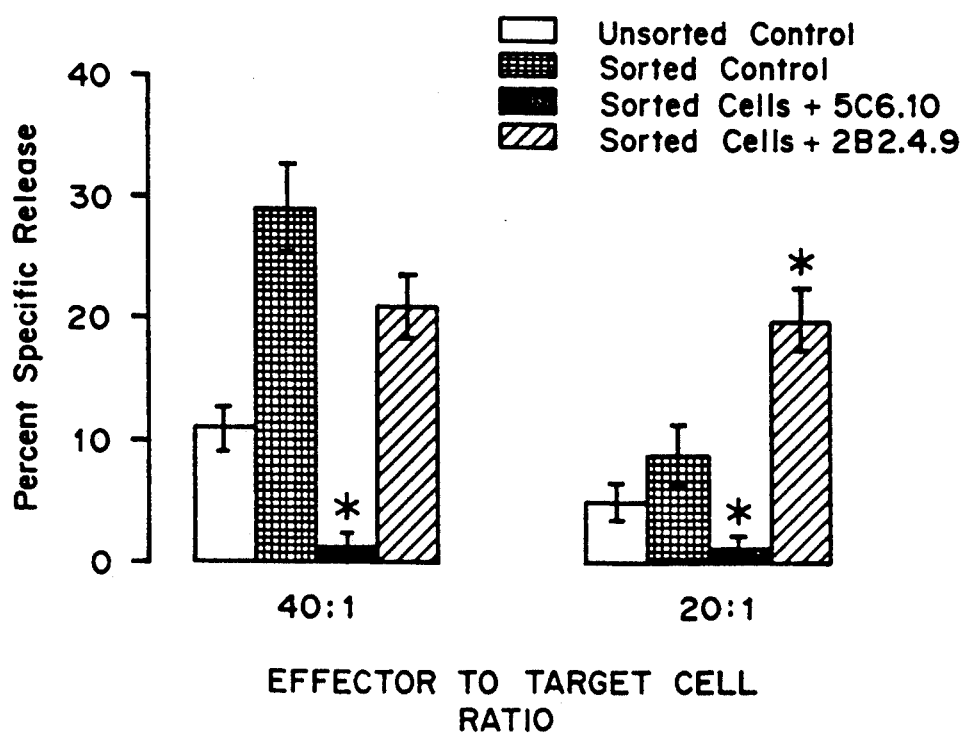
FIG. 2 compares the inhibitory effect of 10 μg 5C6.10.4 and 2B2.4.9 mAb directed against NCC on lysis of anterior kidney cells by NCC in a 4 h assay at 27° C., where sorted effector cells are enriched by flow cytometry, at effector to target cell ratios of 20:1, 40:1.

Next, nonspecific cytotoxic cells were sorted by flow cytometry using the FALS and L90°LS parameters. The sorted cells were incubated with mAbs 5C6.10.4 or 2B2.4.9 and tested for lytic activity (FIG. 2). FIG. 2 shows inhibition of NCC cytotoxicity by addition of Con-A purified mAbs. Unsorted effector cells are unfractionated anterior kidney cells, while sorted effector cells were enriched by flow cytometry. The assay was conducted for 4 hours at 27° C. The number of enriched effector cells necessary for higher E:T ratios was not obtainable. Data are mean and S.D. of three replicates at each E:T ratio. Asterisks indicate significant difference from sorted controls (P=0.001). 10 micrograms of mAb was added to each reaction mixture. Significant (96%) inhibition of lysis of NC-37 target cells was produced at a 40:1 E:T ratio in the presence of 10 micrograms of purified mAb, as well as at a 20:1 E:T ratio.

Effector NCC next were treated with each mAb to determine if inhibition of conjugate formation occurred. Percoll purified NCC ($1.5 \times 10^6$ cells) were treated with 75 or 150 µg of each mAb, the cells were washed and NC-37 target cells were added (1:2 E:T ratio). Compared to NMS (negative control), significant inhibition of conjugate formation was produced by both inhibitor mAbs, but not by the noninhibitor mAbs. A dose response for mAb inhibition of conjugate formation was also observed. Noninhibitor mAbs had no significant effect on the percent conjugates formed. Cytotoxicity experiments conducted indicated that lysis of the target cells was likewise inhibited by both concentrations of 5C6.10.4 and 6D3.2.10 (Table II).

TABLE II

Effects of mAb treatment on NCC conjugate formation with NC-37 target cells

| Monoclonal Antibody | Treatment[c] | Percent Inhibition | |
|---|---|---|---|
| | | Conjugate Formation | Cytotoxicity |
| Media[a] | — | 0 | 0 |
| NMS[b] | (1:200) | 0 | 0 |
| 5C6.10.4 | 75 ugm | 47.28* | 52.87* |
| 5C6.10.4 | 150 ugm | 82.40* | 84.18* |
| 6D3.2.10 | 75 ugm | 46.20* | 48.50* |
| 6D3.2.10 | 150 ugm | 80.22* | 81.15* |
| 2B2.4.9 | 75 ugm | 20.87 | 11.80 |
| 2B2.4.9 | 150 ugm | 8.80 | 5.73 |
| 6D3.4.4 | 75 ugm | 3.27 | 7.10 |
| 6D3.4.4 | 150 ugm | 23.1 | 22.2 |

TABLE II-continued

Effects of mAb treatment on NCC conjugate formation with NC-37 target cells

| Monoclonal Antibody | Treatment[c] | Percent Inhibition | |
|---|---|---|---|
| | | Conjugate Formation | Cytotoxicity |
| 5C6.10.4[d] | 150 ugm | 78.05* | 81.82* |

[a] Media controls contained 34.6 cells bound to NC-37 targets of 300 nontarget cells counted. At an 80:1 E:T ratio, media controls had 38% cytotoxicity by chromium-51 release assay.
[b] A 1:200 dilution of NMS produced 30.3 cell/NC-37 conjugates of 300 nontarget cells counted. At an 80:1 E:T ratio, NMS controls had 29.7% cytotoxicity.
[c] All mAbs were purified by immunoaffinity chromatography as described in the Materials and Methods section. The mAbs were present during the conjugate assay. Monoclonal antibodies were used at either 75 or 150 ugm/1.5 × 10^6 cells.
[d] Positive control consisted of ammonium sulfate purified mAb (e.g. not subjected to immunoaffinity chromatography).
*Significantly different from NMS control (p ≦ 0.05) (one-way ANOVA).

Figure 3:
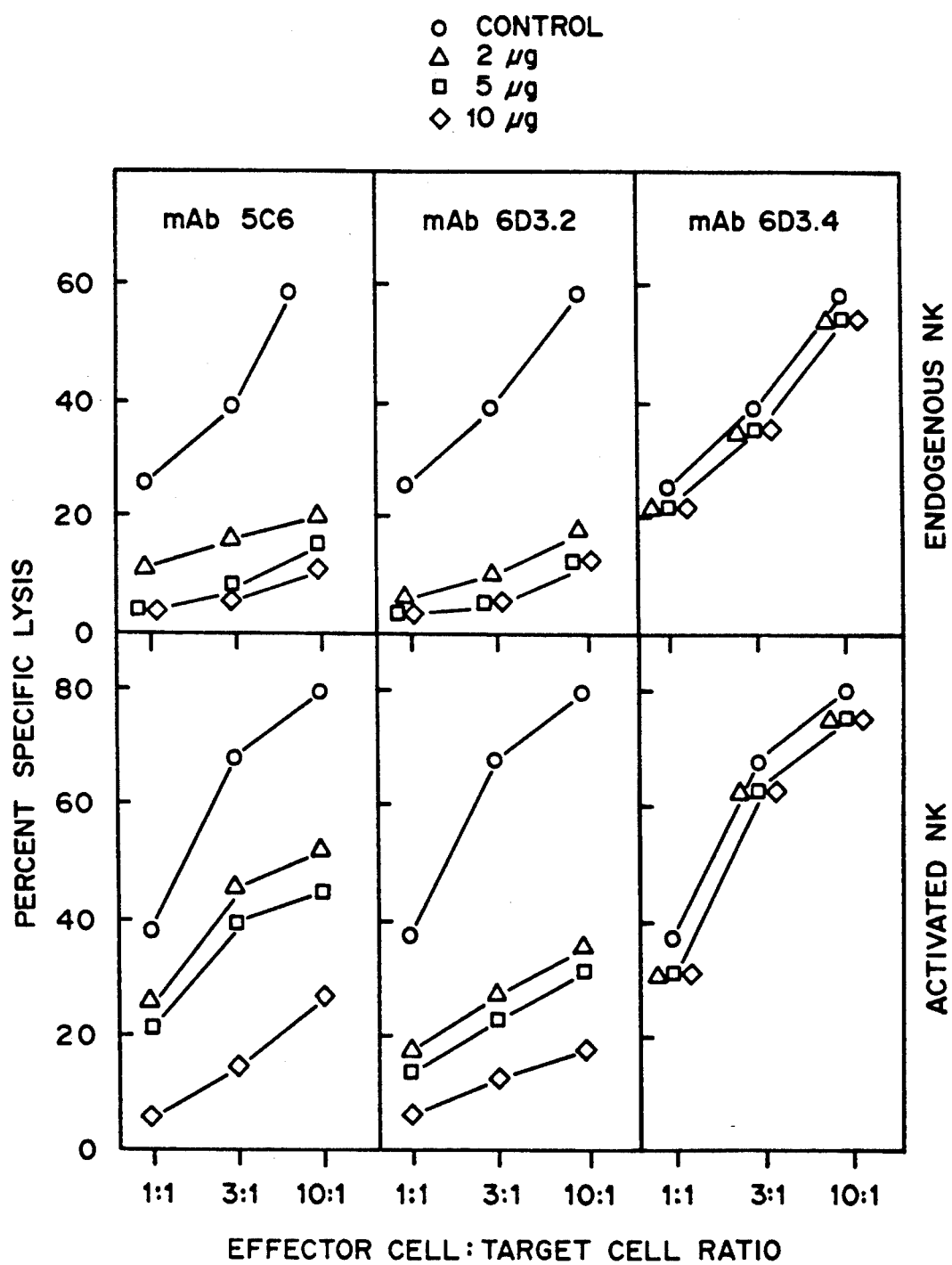
FIG. 3 compares the percent lysis of $^{51}$Cr-labelled K562 targets (10,000 targets/well) incubated with endogenous NK or activated NK cells. Cells were either preincubated with media as a control or with 2, 5, or 10 μg mAb/well for 1 h at 4° C., in a 3 h assay at 37° C., at effector to target cell ratios of 1:1, 3:1, and 10:1. Monoclonal antibodies were 5C6.10.4, 6D3.2.10, and 6D3.4.10.

FIG. 3 shows inhibition of the cytolytic activity of fresh and activated NK cells by anti-NCC monoclonals. Endogenous and IL2-activated NK cells were purified. Each effector cell population was preincubated with the indicated dose of mAb for 1 hr at 4° C. (and washed 2×) prior to addition of K562 target cells. Cytolytic assays were carried out for 3 hr. Percent specific lysis data were converted to $LU_{20}$ and are indicated in parentheses for each curve. Similar results were obtained in two other independent experiments.

All mAbs next were examined for binding to anterior kidney and spleen tissue. The fluorescence histogram of mAbs 5C6.10.4 and 6D3.2.10 binding to anterior kidney cells shows two binding populations, with the concentration of mAb 5C6.10.4 being approximately 10 times higher than cells stained with mAb 6D3.2.10. The same mAb, 5C6.10.4, binds to cells from two different tissues (spleen and anterior kidney). Cells from both of these tissues bound approximately the same amount of mAb. Percent specific staining by each mAb to anterior kidney, spleen and peripheral blood varied according to cell type and mAb. Higher concentrations of 6D3.4.4 bound to cells in each tissue compared to any other mAb. Also, spleen cells bound higher concentrations of each mAb compared to anterior kidney and peripheral blood. Peripheral blood did not bind significant amounts of any mAb.

In assays using unsorted fish anterior kidney cells as effectors, the mAb 5C6.10.4 inhibited NCC lytic activity by 63% (FIG. 2). Similar levels of inhibition were observed when either the NCC were preincubated with the mAbs or when the mAbs were added to the cytotoxicity assay without preincubation. Other studies have been conducted using mammalian NK cells to identify inhibitory mAbs with similar properties of the anti-NCC mAbs. NK inhibitory mAbs were effective when added simultaneously with the effectors and target. Mammalian NK activity can likewise be inhibited by pretreatment of the effectors alone with the mAb prior to assay.

Other assay conditions were examined to better understand the mAb requirements to produce inhibition. As little as 10 μg of purified anti-NCC mAb produces 96% inhibition of cytotoxicity. In a similar study in mice an mAb which inhibited Con-A induced T cell proliferation also inhibited T cell mediated cytolysis by 67% at mAb concentrations as low as 1 mg/ml.

Mechanism of Inhibition of NCC Lysis by mAbs Directed Against the NK Cell Receptor The mechanism(s) of mAb inhibition of NCC was determined by investigating the stage of the lytic cycle at which inhibition occurred. Pretreatment of the NCC with purified mAbs produced significant decreased conjugate formation between NCC and NC-37 targets. Although binding occurs between the noninhibitor mAbs and the effector cells, conjugate formation was not significantly reduced. Other work has shown that mAbs specific for CD45 (T200 family) and CMRF-11, CMRF-12 and CMRF-26 all inhibited NK activity at a post binding stage. Unlike these results, the mAbs of the present invention were shown to react against an antigen binding receptor on NCC. This clearly demonstrated their ability to inhibit the first stage (conjugate formation) of several sequential steps that lead to target cell lysis.

To evaluate the relative concentrations of the membrane determinants found on NCC and to determine the distribution of receptor bearing cells in fish lymphoreticular tissue, FCM analysis was conducted. Both inhibitor and noninhibitor mAbs bound to anterior kidney and spleen cells. NCC were not detectable in peripheral blood by FCM analysis, however. It has been found that there is 16-18% conjugate forming NCC in anterior kidney cells in the presence of NC-37 target cells. By FCM analysis, from 25% (5C6.10.4) to 39% (6D3.4.4) of anterior kidney cells contain the determinants recognized by these mAbs. These differences observed between the single cell in agarose technique and the FCM analysis data obviously reflect the sensitivities of these protocols for detecting NCC.

Isolation and Characterization of the NK Cell Receptor

NCC were sorted by FCM and detergent solubilized extracts of these cells were purified by affinity chromatography (Affigel 15 TM) using mAb. The same dimer was purified using either inhibitory (6D3.2.10) or noninhibitory (6D3.4.4) mAbs. The purified proteins comprise two bands by SDS analysis. Both the inhibitory and noninhibitory mAbs precipitated 2 proteins, one with a molecular weight of approximately 41,000 D and a second of approximately 38,000 D. This complex consists of 41,000 and 38,000 D molecules which comigrate as two separate chains regardless of the presence of nonreducing or reducing agents. Molecules with this characteristic have not been reported previously for any type of effector of "non-specific" cytotoxicity (e.g., NK, anomalous killer, promiscuous killer, LAK, CTL-NK, etc.).

Similar results were obtained with immunoprecipitation experiments using mAb 5C6.10.4 and analyzed by SDS-PAGE under reducing conditions. The precipitated 43,000 D and 38,000 D molecules were similar to those observed with affinity chromatography.

The proteins and antibodies of the present invention have uses in addition to providing information regarding their origin and function. They can be used in assays to screen for related or altered proteins. They can be used, alone or in combination with biologically active compounds, for treatment of disease states including cancer and autoimmune diseases. Such uses are intended to come within the scope of the present invention. The proteins of the present invention, both the antigen and the receptor, can be further characterized by studies involving the extent and function of carbohydrate on the molecules, the rate of turnover on the cell surface, the isoelectric points, the relationship and homology between the dimer subunits, and the effect of modifications thereof on biological function. Modifications to the proteins chemically as well as by production of mutants can be used to achieve the latter. Methods to produce this information are available to those skilled in the art and are described in detail herein.

Since the proteins have been purified to homogeneity as measured by SDS-PAGE, it is possible to sequence the molecules so as to compare the sequences with known molecules and to prepare nucleotide probes for screening of libraries for sequences encoding the molecule. The probes are also useful in measuring mRNA content in the various low and high expression cell lines and mutants to determine at what level, mRNA processing or protein assembly, that the changes occur. Alternatively, the clones can be screened using the mAbs described above or heterologous antisera raised to the purified proteins. cDNA libraries are available from a number of cell lines. They can also be prepared as required using an expression vector such as lambda gt11 using poly(A) RNA isolated from effector or target cell lines. Positive clones can be rescreened to homogeneity at low density and compared with one another by restriction mapping and Southern blot analysis to identify identical or overlapping clones. The sequencing data from the identified clones can be used to provide further support and means for identification of the genes for either the receptor or the antigen, and aid in identification of related molecules. Further, these sequences and probes can be used in assays to characterize immune cells and target cells according to their receptor or antigen. As importantly, identification and characterization of the sequences and their respective function provides a means for modifying relationships in vivo, either enhancing or inhibiting the cytolytic activity of natural killer cells against target cells or even cells which would not normally serve as targets for the natural killer cells. The sequences could also be used to map the location of the genes for these proteins on the chromosomes, allowing screening for potential defects in the immune response, either congenital or disease or environment induced. Knowledge of the genes encoding these molecules also provides information on the regulation of expression and function of these proteins, information not presently available for any molecule within the immune system which is common to so many different species of such wide evolutionary divergence. Methods to accomplish these ends are presently available to those skilled in the art once the proteins and sequences or probes for sequences encoding these proteins are known. The sequences, probes, and uses therefore are intended to come within the scope of the present invention.

MATERIALS AND METHODS

Animals

Outbred channel catfish (*Ictalurus punctatus*) of both sexes, weighing 10 to 25 grams, approximately 6 months to one and one-half years of age were obtained from local commercial farms. Fish were maintained in 570 liter fiberglass running streams at temperatures ranging from 16°-19° C. The diet consisted of pelleted fish feed (Purina Catfish Startena, Ralston-Purina Co.). Balb/c mice were used for mAb production and were purchased from Harlan Sprague-Dawley (Indianapolis, Ind.).

Media

Cell cultures were maintained in RPMI-1640 (Flow Laboratories, Rockville, Md.) adjusted to an osmolarity of 250 milliOsmoles/kg $H_2O$ using a micro-Osmette (Precision Systems, La Jolla, Calif.).

Preparations of Cell Suspensions

Fish were lightly anesthetized with ethyl-aminobenzoate (Sigma Chemical Co., St. Louis, Mo.) in water and sacrificed. Anterior kidney, peripheral blood and spleen cells were removed and single cell suspensions prepared, as described by S. S. Graves et al., *Dev. Comp. Immunol.* 8,293 (1984), the teachings of which are incorporated herein. Cells were washed twice ($200 \times g$; 10 min), stained with trypan blue and counted in a hemocytometer. Samples for flow cytometric analysis were adjusted to $2 \times 10^6$ total cells/ml. Erythrocytes were removed by preparing a solution of phosphate-buffered saline (250 milliOsmoles/kg $H_2O$) and Percoll ® (Pharmacia Fine Chemicals, Inc., Uppsala, Sweden). This solution was added in 2 ml volume to 15 ml plastic tubes. A suspension of anterior kidney, peripheral blood or spleen cells ($3 \times 10^8$ cells/ml) was layered in 1 ml volumes on the Percoll ® solution. The tubes were centrifuged ($300 \times g$ for 10 min) and the leukocytes withdrawn from the interface and washed ($2 \times$). For effector cell preincubations, cells were suspended at $2 \times 10^7$ cells/ml in RPMI-1640 (10% FBS) and incubated for 4 hr in 24 well tissue culture plates (Linbro Plastics, Flow Laboratories, McLean, Va.) at 26 C and 5% $CO_2$ tension.

Production of Monoclonal Antibody Directed Against Receptor Protein

The myeloma cell line $P_3$-X63-$Ag^8$ ($P_3$) was cultured in complete RPMI-1640 media containing 10% heat inactivated FBS. Spleens were aseptically removed from mice previously immunized with FCM sorted NCC, as described by D. L. Evans et al in *Dev. Comp. Immuno.* 11,95 (1987), the teachings of which are incorporated herein on target cells, as described below, and washed ($2 \times$) in RPMI-1640 (without serum). Spleen cell suspensions were mixed with $P_3$ cells (logarithmic growth). Cells were washed ($3 \times$) counted and mixed at a ratio of $5.0 \times 10^6$ spleen cells to $1.0 \times 10^6$ myeloma cells. Cell fusion was accomplished using 1.0 ml of polyethylene glycol (BMB Biochemicals Indianapolis, Ind.). After the fusion step, cells were centrifuged ($220 \times g$, 10 min), the supernatant was removed and the cells resuspended in 40 ml of complete RPMI (15% FBS). The cell suspension was divided equally ($2.5 \times 10^6$ cells/ml) into the wells of a 48-well plate and incubated overnight at 37° C. in 5% $CO_2$ tension. The media was then changed to complete RPMI-1640 supplemented with 15% FBS and 0.1 mM hypoxanthine, $4.0 \times 10^{-7}$M aminopterin and $1.6 \times 10^{-5}$M thymidine (HAT medium). The HAT medium was replenished (50% substitution by volume) on day 7 after the fusion. On day 10 the HAT medium was replaced by complete RPMI medium supplemented with 0.1 mM hypoxanthine and $1.6 \times 10^{-5}$M thymidine (HT medium). Culture medium was thereafter replenished as necessary. Supernatants containing growing hybridomas were then screened by ELISA.

Production of Monoclonal Antibodies Directed Against the Antigen on Target Cells The cells used for anti-target cell antigen mAb production were the NC-37 human lymphoblastoid B-cells. This cell line carries EBV genomic sequences, however, EBV membrane antigens are not expressed. The following cell lines were also used in cytotoxicity assays: DAUDI (human lymphoblastic B-cell), MOLT-4 (human leukemic T-cell), HL-60 (human promyelocytic leukemic cell), K562 (human erythromyeloid leukemia), U937 (human histiocytic leukemia), P815 (mouse mastocytoma), and YAC-1 (mouse lymphoma induced by Moloney Leukemia virus). All cell lines were maintained in vitro at 37° C. in RPMI-1640 containing 10% FBS. *Tetrahymena pyriformis* (Midwest Culture Service, Terre Haute, Ind.) was cultured in Elliott's medium in 500 ml flasks.

NCC Solubilization for Receptor Isolation

Nonspecific cytotoxic cells were washed twice in PBS (pH 7.5), resuspended at $5 \times 10^8$ cells/ml, and solubilized by addition of 5.0 ml of 20 mM Tris-HCl at pH 7.5, containing 1 mM phenylmethylsulfonyl fluoride and 1% Nonidet-P40. After two hours (4° C.) the sample was centrifuged (100,000×g; 60 min) and the supernatant dialyzed against PBS for 48 hrs (4° C.) and stored at $-20°$ C. Cell extracts (7 micrograms) of each sample were electrophoresed in 12.0% SDS-PAGE; 5 hr at 15 milliamps. Gels were stained using a standard silver nitrate technique (Bio Rad Laboratories, Richmond, Calif.)

Isolation of Anti-Receptor Antibodies

Hybridomas from the fusions between P3 myeloma cells and immune spleen cells from Balb/c mice immunized with FCM purified NCC were screened using an ELISA technique. The ELISA plates were coated with NCC preparations obtained from anterior kidney tissue. For this, NCC were used which had been enriched approximately 5-6× on 45.5% Percoll ®. ELISA positive hybridomas were tested for inhibition of NCC lysis of $^{51}$Cr-labeled NC-37 target cells. Of the ELISA positive mAbs tested, four mAbs were chosen for further study. These were designated 5C6.10.4, 6D3.2.10, 6D3.4.4, and 2B2.4.9, respectively. All four mAbs are IgM and all were subcloned two times by limiting dilution.

Production of Anti-NC-37 (Antigen) Monoclonal Antibody

Mice were immunized intraperitoneally with $5 \times 10^6$ NC-37 cells in RPMI 1640 and boosted after one week (IP) with the same number of cells. Three days prior to fusion, the mice were again boosted with NC-37 cells and their spleen cells fused with murine P3-X63-Ag8.653 myeloma cells at a 2:1 ratio, using polyethylene glycol (MW 3,350, Sigma Chemical Co., St. Louis, Mo.). Cells ($1 \times 10^6$) were seeded into 24 well plates and their supernatants were screened using a two-step protocol consisting of NC-37 and Tetrahymena enzyme-linked immunoabsorbent assays (ELISAs). Wells were coated with $5 \times 10^8$ NC-37 or Tetrahymena cells and stored at $-70°$ C. Cells from supernatant positive wells were transferred to 25 cm$^2$ tissue culture flasks, expanded, subcloned twice by limiting dilution, and the positive clones were isotyped and stored at $-70°$ C. For purification, cloned hybridomas were injected into pristane-treated Balb/c mice, the ascitic fluid was collected, heat inactivated (60 min at 56° C.), and filter sterilized. The 50% ammonium sulfate precipitated mAbs were further purified by Con A Sepharose (IgM mAbs) or Protein A Sepharose (IgG mAbs) chromatography.

mAbs were chosen on the basis of their ability to inhibit target cell killing.

The fusions were screened using NC-37 and Tetrahymena ELISAs. Four different target cell reactive mAbs were chosen for further characterization. These mAbs were designated as 1E7.4.7, 18C2.8.3, 1D4.5.8, and 7C6.5.4. The specificity of each of the monoclonal antibodies was tested by pretreating them with either BSA, P3 ascites fluid, P3 supernatant, or NC-37 whole cells, prior to their addition to NC-37 or Tetrahymena coated ELISA plates. Inhibition of the binding of mAbs 18C2.8.3, 1E7, and 1D4 was observed only upon preincubation of these monoclonal antibodies with NC-37 cells, while the other treatments did not cause a decrease when compared to control levels (no treatment). The reactivity of mAb 7C6.5.4 as measured by binding to ELISA plates was not altered by any of the treatments.

Concanavalin A Sepharose Chromatography of mAbs

IgM monoclonal antibodies were purified by affinity chromatography according to the method of M.D.P. Boyle et al in *J. Immun. Methods* 32,51 (1980) utilizing Con A Sepharose beads (Affigel Con-A, BioRad Labs, Richmond, Calif.). The Concanavalin A Sepharose gel was washed with 3-5 bed volumes of sample application buffer (containing 10 mM Tris [pH 7.2], 1 mM Mg$^{++}$, and 1 mM Ca$^{++}$). After removing excess buffer above the gel, 2-5 ml of sample was applied and mixed very gently, forming a slurry. The column was then washed with the application buffer, and samples monitored until the O.D. (280 nm) of the effluent was the same as the application buffer. The specifically bound IgM mAbs were then eluted with 200 mM alpha-D-methyl mannopyranoside. The gel was regenerated by washing with 3-5 bed volumes of the application buffer, and was stored at 4° C.

Cytotoxicity Assay

Cytotoxic activity was measured using a $^{51}$Cr-release assay as previously described by Graves et al., (1984). The NC-37 human lymphoblastoid B cell line was used as a target. These cells were maintained in RPMI-1640 (10% FBS) at 37° C. and 5% CO$^2$ tension. Target cells were labeled with 100 $\mu$Ci of $^{51}$NaCrO$_4$ (Amersham Corporation, Chicago, Ill.) for 2 h at 37° C. as described by Graves et al. Fish NCC were assayed using head kidney cells prepared as single cell suspensions, washed twice, counted, and incubated for 4 h at a concentration of $2 \times 10^7$ cells/ml in RPMI 1640 containing 10% FBS. Following this preincubation period, NCC were harvested, centrifuged, and added to $^{51}$Cr-labeled target cells at different effector: target cell ratios. To assess cytotoxicity, 100 microliters of supernatants were harvested from each well and radioactivity was determined in a Beckman Biogamma II gamma counter. Cytotoxicity was expressed as percent specific release (% SR) and calculated using the following formula:

$$\% SR = \frac{(\text{test release}) - (\text{spontaneous release})}{(\text{total incorporation}) - (\text{spontaneous release})} \times 100$$

Flow Cytometric Analysis

An EPICS V$^R$ 753 flow cytometer (Coulter Electronics, EPICS Division, Hialeah, Fla.) was used to analyze cell size, granularity, and fluorescence. Samples of viable cells were prepared at a concentration of $2\times10^6$ cells/ml and analyzed by forward angle light scatter (FALS), $Log_{10}$ 90° light scatter (L90°LS), or green fluorescence. The instrument was standardized daily using Fulbright (GR II) 9.75 micrometer diameter fluorescent polystyrene microspheres and operated at constant laser power and photomultiplier settings. The green fluorescence PMT received light after passage through a 488 nm laser blocker and a 525 nm bandpass interference filter. Analyses were performed using a flow rate of 300–400 cells/second. The FALS and L90°LS parameters were used to electronically gate the lymphocyte population to exclude debris and to enable analysis of negative cells. All analysis was done using an argon-ion laser (488 nm emission) at a constant power of 500 mW.

For all sorting, the sheath buffer (normal saline) was adjusted to 250 mOsm/kg $H_2O$ and cells were sorted based on previously established parameters of FALS and L90°LS. Fluorescence analysis was accomplished using FITC conjugated anti-mouse IgM antibodies (Sigma Chemicals, St. Louis, Mo.). Cells were excited at 488 nm and fluorescence was detected using a 590 nm (short pass) dichroic mirror and a 525 nm band pass interference filter. Two different electronic gating procedures were used: for analysis of percent specific binding, FALS and L90°LS gating was used; and to obtain optimal histograms, gating was done based on the $LOG_{10}$ green fluorescence signal.

To determine mAb binding, cells were harvested from the anterior kidney and spleen as previously described and resuspended at 1 to $2\times10^6$/ml in RPMI media. Each monoclonal antibody to be tested was added (100 micrograms) to 0.5 ml of the cell suspension and incubated 30 min (4° C.). Normal mouse serum or irrelevant IgM monoclonals were used as controls. Cells were washed two to three times in cold (4° C.) RPMI-1640. Fluorescein isothiocyanate conjugated anti-IgM or anti-mouse IgG (Sigma Chemical Co., St. Louis, Mo.) (1:20 dilution) was added in 100 µl. The cells were again incubated on ice for 30 min, washed twice in cold (4° C.) media and resuspended in 1 ml media for flow cytometric analysis.

Conjugate Assay

To prepare cells for the assay, anterior kidney cells were isolated, washed, and fractionated by layering over 45.5% Percoll$^R$ (3 ml of cells on 6 ml Percoll). After centrifugation for 20 minutes at $200\times g$, the cells at the media—Percoll interface were harvested, washed and counted. $70\times10^6$ cells/ml were then incubated for 6 hours (25° C.).

To prepare Percoll purified NCC for the conjugate assay, $7.5\times10^5$ cells were dispensed into each tube and appropriate media, NMS or purified mAb was added (total volume of 375 µl). The cells were incubated for 60 minutes (5% $CO_2$, 25° C.), centrifuged ($200\times g$) and resuspended in 375 µl of RPMI-1640.

The single cell in agarose conjugate procedure was conducted as previously described for fish NCC by Evans et al (1984). Briefly, 100 µl of treated NCC ($2\times10^6$ cells/ml) and 200 µl of NC-37 ($2\times10^6$ cells/ml) cells were mixed in round bottom glass tubes and incubated for 5 minutes (30° C.). The cells were then centrifuged for 5 minutes ($200\times g$), the pellet gently resuspended into 50 µl of premelted agarose and then the mixture poured onto agarose precoated slides. To determine percent conjugates, 300 effector cells were counted and the number of effectors bound to NC-37 cells were determined. Coded samples were counted (single-blind analysis).

Affinity Chromatography of Receptor

For purification of the receptor, Con A Sepharose purified monoclonal antibodies 6D3.2 and 6D3.4.4 were coupled with Affi-gel 10 TM (Bio Rad, Richmond, Calif.) at a concentration of 5 mg of protein/ml of gel for 4 hr at 4° C. with gentle shaking in 10 mM Hepes buffer (pH 7.5). The reaction was stopped by centrifugation and the gel was resuspended in 0.1M glycine ethyl ester (pH 8) for one hr to block the remaining active sites. After repeated washes with PBS (pH 7.5), the gel was stored at 4° C. Solubilized NCC lysates were incubated with 6D3.2 and 6D3.4.4 affinity gels at a concentration of 2 mg protein/ml of beads overnight at 4° C. with gentle shaking. The gels were poured into two columns and washed extensively with PBS (pH 7.50) until eluted proteins could not be detected at $OD_{280}$. Specific effector cell (NCC) antigens were eluted with glycine/HCl buffer (0.1M adjusted to pH 2.5 with 0.2M HCl) until all protein was eluted. Fractions were collected into tubes containing 100 µl of 1M Tris HCl, pH 8.0. The peak fractions were pooled, dialyzed against PBS, concentrated using carboxymethyl cellulose and stored at $-20°$ C.

Immune Precipitation and SDS-PAGE Analysis of the NCC Receptor

Fish NCC lysates were precleared with a 12 hour incubation with Sepharose CL4B beads at 4° C. The precleared lysate then was incubated with Protein A Sepharose 4B bound to mAb 5C6.10.4 for 4 h at 4° C. The Protein A-Sepharose 4B complex was washed ($3\times$) with 1% Triton X-100 buffer. The specifically bound molecules then were eluted with $2\times$ sample buffer (125 mM Tris-HCl, pH 6.8 with 20% glycerol (v/v), 4% SDS (w/v)) and 10% beta-mercaptoethanol (v/v) and samples were electrophoresed (11% SDS-PAGE). The gels were stained by the silver stain method (Bio Rad Laboratories, Richmond, Calif.).

Statistical Analysis

Probability statements were obtained by one-way analysis of variance (ANOVA).

Analysis of NC-37 Cell Lysates by Western Blot

NC-37 cells were washed twice with PBS (pH 7.5), resuspended at $5\times10^8$ cells/ml, and solubilized by addition of 5.0 ml of 20 mM Tris-HCl (pH 7.5) containing 1 mM phenylmethylsulfonyl fluoride and 1% Nonidet-P40. After two hours (4° C.) the sample was centrifuged ($100,000\times g$; 60 min) and the supernatant dialyzed against PBS for 48 hrs (4° C.) and stored at $-20°$ C. All homogenates were electrophoresed in 10% sodium dodecylsulfate polyacrylamide gels (SDS-PAGE). Samples were transblotted onto nitrocellulose paper (12 hours at 100 mAmps followed by 2 hours at 320 mAmps at 4° C.). The lane containing the molecular weight standards was cut and stained with Amido Black to determine total protein. The nitrocellulose membrane (containing the transferred protein) was immersed in 50 mM Tris-HCl, 5% Carnation Nonfat Dry Milk, 0.9% NaCl and 0.05% Tween-20 at pH 7.6 (blocking buffer) for 2 h and then cut into 1 cm strips. The strips were incubated with the mAb for 90 min followed by a 60 min incubation period with horseradish peroxidase conjugated goat anti-mouse IgG, IgA, IgM (Cappel Biomedical, Malvern, Pa.). After washing in blocking buffer, the substrate (HRP Color Development Solution, Bio Rad Laboratories, Richmond, Calif.) was added and the color development was stopped by immersion in dH$_2$O for at least 10 min.

Immunoprecipitation of the Receptor

Labeled cells are resuspended in buffer to 2–4×10$^7$/ml. An equal volume of lysis buffer (1% NP40; 1% BSA; 1 mM PMSF) is added. Nuclei, debris and unlysed cells are removed by centrifugation at 3,000×g for 15 min. Immune precipitation is carried out as follows: Labeled cell extract is mixed with the appropriate mAb in a buffer containing 0.01M Tris, pH 7.5, bovine serum albumin (100 μg/ml) and 0.3% Triton X-100. Incubation is for 3 h at 4° C. Staphylococcal protein-A is added (10%), v/v) to the antigen-antibody mixture, and incubated for 1 h at 37° C. This mixture is centrifuged (200×g, 2 min, 4° C.) and the pellet treated by adding 50 μl of SDS buffer (3% SDS/2% mercaptoethanol/0.05 Tris, pH 6.8/5% glycerol) followed by boiling 10 min and centrifugation. Alternatively, the staphylococcal protein-A antigen-antibody mixture is suspended in 4% SDS in 8M urea (containing 0.05M Tris, (pH 8.4), boiled 3 min and centrifuging (2000×g, 6 min). In each immune precipitation, labeled antigen will always be in excess.

Immunoprecipitation and SDS-PAGE Analysis of the NC-37 Target Antigen

NC-37 cells were incubated for 6 hours with 100 μCi/10$^6$ cells/ml $^{35}$S-methionine (New England Nuclear, Boston, Mass.). The labeled cells were centrifuged and lysed with 1% Triton X-100 buffer (0.15M NaCl, 1% NaDOC, 1% Triton X-100, 10 mM Tris, pH 7.4, 1 mg/ml BSA, 0.02% NaN$_3$, 0.1 mM PMSF). Nuclei were removed by centrifugation and the supernatant was precleared (12 h) with Sepharose CL 4B beads (4° C.). The precleared lysate then was incubated with Protein A Sepharose 4B bound to mAb 18C2.8.3 or 1E7. The Protein A Sepharose 4B complex next was centrifuged and washed (3X) with the above buffer, the mAb purified target cell antigens were eluted with 2X sample buffer (125 mM Tris-HCl pH 6.8 with 20% glycerol v/v, 4% SDS w/v and 10% betamercaptoethanol v/v) and samples were electrophoresed (11% SDS-PAGE). The gels were dried and exposed to X-ray film (X-OMAT, KODAK, Rochester, N.Y.) for 5 days at room temperature.

Immune precipitation of the NK Cell Antigen was performed as for the receptor.

Phycoerythrin-B Conjugation

Thiolated phycoerythrin is prepared by the addition of 600 μl of 15.5 mg/ml iminothiolene hydrochloride (Sigma Chemical Co.) to 1.2 ml of 3.6 mg/ml phycoerythrin-B in 125 mM sodium phosphate (pH 6.8). After 90 min at room temperature, the reaction mixture is dialyzed overnight at 4° C. against 50 mM sodium phosphate (pH 6.8) and then for 2 days against pH 7.5 buffer (this gives an average of 8-SH-groups/molecule).

A 30 μl aliquot of 1.1 mg/ml N-succinimidyl 3-(2-pyridylthio-proportionate (SPDP) (Pharmacia Fine Chemicals, Piscataway, N.J.) in ethanol is added to 700 μl of 4.2 mg/ml immunoglobulin in 50 mM sodium phosphate (pH 7.5). The molar ratio of SPDP to IG is 5.3. The reaction is allowed to proceed for 2.5 h at room temperature. Thiolated phycoerythrin (400 μl of 1.7 mg/ml in the same buffer) is added to 500 μl of the reaction mixture. The molar ratio of activated Ig to thiolated phycoerythrin-B is 4.7. After 12 h at room temperature, 100 μl of 80 mM sodium iodoacetate is added to block any remaining sulfhydryl groups.

Phorbol Ester Treatment

Phorbol-12-myristate-13-acetate (PMA) and its analog 4-alpha-phorbol-12, 13-didecanoate (4-alpha PDD) (an inactive analog of PMA), is used to determine the effects of phorbol esters on NCC/NK lytic activity. NCC and NK cells are treated with PMA (10$^{-6}$M) or with 4 alpha PDD (10$^{-6}$M). Cells are treated from 1 h to 40 h to determine the effects of these substances on effector cell activity, and on the membrance expression of the effector cell receptor. Increased expression of the monoclonal reactive determinants is determined by FCM and by increased (or decreased) lysis of susceptible target cells.

RadioLabeling of Surface Carbohydrate

Sialic acid residues of glycoproteins are labeled by tritiated sodium borohydride, NaB$_3$H$_4$, reduction of oxidized carbohydrates. One to two×10$^7$ lymphocytes in 1 ml of PBS are incubated for 10 min at 0° C. with 1 mM sodium periodate for the formation of aldehyde groups on the sialic acid residues. The reaction is stopped by the addition of glycerol to a final concentration of 25 mM and the cells are washed twice with PBS. The pelleted cells are resuspended in 0.5 ml of Dulbecco's balanced salt solution (DBSS) and 1 mCi of NaB$_3$H$_4$ is added to reduce the aldehyde groups to their corresponding alcohols. The mixture is incubated for 30 min at room temperature and washed twice with DBSS.

Human NK Cells

Heparinized peripheral blood is obtained from normal donors (aged 18–30 years) as a source of NK cells. Peripheral blood lymphocytes (PBL) are centrifuged over Ficoll-Hypaque gradients as taught by Boyum, *Scan. J. Clin. Lab. Invest.* 21 (Suppl. 97),9 (1968) to obtain mononuclear cells (MNC). MNC are enriched for NK activity by one or a combination of the following techniques: (a) MNC are plated on plastic petri dishes for 2 cycles of 1 h at 37° C. and the nonadherent cells carefully collected PNAd; Fischer et al, *Cell. Immunol.* 58,426 (1981); (b) PNAd are passed over nylon wool columns and nonadherent cells collected according to Julius et al, *Eur. J. Immunol.* 3,645 (1973); (c) PNAd are centrifuged over Percoll gradients according to the method of Storkus and Dawson, *J. Leukocyte Biol.* 39,547 (1986); and (d) PNAd are panned over mAb PKT3 coated petri dishes and the nonadherent cells collected. Cell viability is assessed by Trypan blue dye exclusion. The various NK populations are phenotyped for the NK markers Leu 11, Leu 7, Leu 19 by flow cytometry.

Culture and Cloning of NK Cells

NK cells isolated by the above methods are the source of cells for bulk culture and cloning. Bulk cultures are grown in 25 mm$^2$ flasks and culture growth initiated by stimulation with either lectins, IL2, irradiated tumor cells or a combination of these stimuli. Irradiated feeder cells are also added. Cultures are maintained by the weekly addition of IL2 alone. The original stimuli and feeder cells are re-added only if growth of the cultures declines. Irradiated B cell lines have been found to serve as feeder cells for human NK cultures. Cultures are screened weekly for phenotype and only typical NK cultures maintained. NK cells are cloned by limiting dilution at 0.25 cells/well in 96 well microtitre plates as described by Van de Griend et al, *J. Immunol. Methods* 66,285 (1984). The clones are expanded as necessary to 25 mm$^2$ flasks and periodically screened for their phenotypes. Up to $100 \times 10^6$ cells can be obtained per clone with this protocol.

Stimulation of NK for Lymphokine Production $1-2 \times 10^6$ NK cells/well are plated in 1.0 ml of complete medium in 24 well Costar plates. The appropriate stimuli are added and the reactions incubated for 24 h at 37° C. Afterwards the wells are harvested and the cells removed by centrifugation (1100 $\times$ g, 10 min). The supernates are sterilized by filtration (0.2$\mu$, Millipore) and stored at 4° C. until analysis. The following stimuli are utilized: IL-2 (30 units/ml), Con A (5 $\mu$g/ml), PHA (1 $\mu$g/ml), and antigen tumor cells, 1:1 NK to tumor cell ratio, attached via poly-l-lysine to the wells and fixed with 0.025% glutaraldehyde for 5 min at 23° C. Complete medium alone serves as a control for spontaneous lymphokine secretion.

Flow Cytometric Analysis of Cellular DNA Content and Distribution

Analysis of DNA content and distribution of NK cells following experimental manipulation will be done. Washed and resuspended NK cells ($1 \times 10^6$ cells/ml in PBS) containing 10 $\mu$g/ml of the DNA-binding dye Hoechst 33342 and 0.1% Nonidet P-40 detergent will be analyzed using a fluorescence-activated cell sorter (FACS). For this, the laser is adjusted to emit 50 mW at 351 and 363 nm. Fluorescence is detected without any intervening optical filters. Narrow angle forward light scatter is used to identify viable cells. $G_0/_1$, S, and $G_2+M$ populations are identified on the basis of fluorescence intensity. A semiquantitative method is used to estimate the relative number of cells in the different phases of the cell cycle (Harris and Sekaly, *J. Immunol.* 133(1), 40 (1984). The $G_0/_1$ and $G_2+M$ phase populations are assumed to be normally distributed and the mean fluorescence intensities determined directly from the DNA distribution. Standard deviations (SD) are calculated by dividing the full width at half-maximum of each peak by 2.35. The $G_0/_1$ population is defined as the region of DNA distribution within 2 SD above and below the mean fluorescence intensity of the $G_0/_1$ peak. The $G_2+M$ population is similarly ascribed to the region of distribution within 2 SD of the $G_2+M$ peak. S-phase cells are defined as having flurorescence intensities distributed between the $G_0/_1$ and $G_2+M$ regions.

NK Radioisotope Labeling and Experimental Protocols

Changes in phospholipid metabolism after stimulation of the NK are determined as follows. NK are collected, prepared and then washed once with labeling buffer (137 mM NaCl, 2.7 mM KCl, 1.0 mM MgCl$_2$, 1.0 mM CaCl$_2$, 20 mM HEPES, 25 mM glucose, 1 mg/ml bovine serum albumin, pH 7.4), resuspended at $20 \times 10^6$ cells/ml in labeling buffer and prelabeled with 50 $\mu$Ci/ml $^{32}$p-orthophosphate (Amersham, 200 mCi/mMol) for 1-2 h at 37° C. in order to equilibrate the cellular ATP pools. At the same time the cells are prelabeled with 20 $\mu$Ci/ml $^3$H-myo-inositol (Amersham, 15 Ci/mMol) as a tracer for the identification of the various inositol lipid species. At the end of the prelabeling time period the cells are either washed twice with labeling buffer and resuspended to $6 \times 10^6$ cell/ml in the same buffer (for short-term assays), or are immediately diluted to $6 \times 10^6$ cells/ml with labeling buffer containing additional radioisotopes ($^{32}$p and $^3$H-inositol) to prevent depletion of $^{32}$P-labeled ATP and trace-labeled inositol pools (for long-term assays). All reactions are carried out in 0.5 ml aliquots ($1.5 \times 10^6$ NK total) at 37° C. Short-term reactions are performed in polypropylene tubes using a 37° C. water bath. Long-term reactions are performed in polypropylene tubes, except for antigen stimulus in which the tumor cells were attached to poly-1-lysine-treated wells of a 12-well Costar plate and glutaraldehyde-fixed prior to the addition of the NK in a humidified 37° C. CO$_2$ incubator. All stimuli are added to the NK while on ice. Reactions are initiated by placing the NK at 37° C., except for short-term antigenic stimulation in which the NK and tumor cells are centrifuged together for 2 min. at 1000 rpm, 4° C. to initiate conjugate formation immediately prior to being placed at 37° C. Reactions are terminated by the addition of 1.95 ml of chloroform/methanol/conc. HCl (100:200:1, v/v) with immediate vortexing of the samples.

To analyze for kDAG generation the cells are labeled for 24 h with 1 $\mu$Ci/ml $^3$H-arachidonic acid (Amersham, 130-200 Ci/mmole). The NK are prepared and the reactions are initiated and terminated as described above for phospholipids analysis.

For IP analysis the NK, $20 \times 10^6$/ml are incubated for 4-5 h at 37° C. in labeling buffer containing $^3$H-myo-inositol (14-20 Ci/mmol) at a concentration of 10 $\mu$Ci/ml. Afterwards NK are washed twice in labeling buffer and resuspended to a final concentration of $60-80 \times 10^6$ NK per ml in the same buffer (4° C.) containing lithium chloride (10 mM). Reactions are initated as described above and terminated by the addition of 1 ml of a 11.25% solution of trichloroacetic acid (TCA) at 4° C. The samples are mixed by vortex and held at 4° C. for 20 min prior to storage at $-70$° C.

Analysis of NK Lipid Metabolism

NK lipids are extracted by the further addition of 0.65 ml chloroform and 0.65 ml 0.1N HCl to the chloroform/methanol-terminated reactions mixtures. The reaction samples are mixed by vortex and centrifuged (2000 rpm 10 min, 4° C.) prior to collection of the organic layers. The samples are then re-extracted with 1.0 ml chloroform and the two organic phases are combined and stored at $-70$° C. until analysis. Prior to thin layer chromatographic (TLC) analysis the samples are evaporated to dryness at 37° C. under nitrogen. TLC analysis is performed using 20 cm $\times$ 20 cm, 0.2$\mu$ silica plates (Silica gel 60, Merck) which have been pre-activated for 1-2 h at 110° C. immediately prior to use. The dried samples are dissolved in 10 $\mu$l of chloroform and applied to the TLC plates. This procedure is then repeated for each sample. 90% or more of the total radioactivity per sample is transferred to the TLC plate. The plates are then reheated at 110° C. for 10 min prior to development.

The lipids are analyzed by ascending TLC in each of the following one-dimensional systems. System I consists of chloroform/methanol/petroleum ether/glacial acetic acid/boric acid (48:24:36:12:2.16, v/v/v/v/w) which separates the following lipid classes in ascending order: lysophosphatidylcholine (LPC), sphingomyelin (SM), phosphatidylcholine (PC), phosphatidylinositol (PI), phosphatidylserine (PS), phosphatidylethanolamine (PE), phosphatidic acid (PA), free fatty acids (FFA) and triglycerides (TG). System II consists of chloroform/acetone/methanol/glacial acetic acid/water (40:15:13:12:8 by volume) and utilizes 1% di-potassium oxalate (in methanol/water, 2:3)-treated TLC plates. System II resolves the following lipid classes in ascending order: phosphatidylinositol-4,5-biphosphate (PIP$_2$), phosphatidylinositol-4-monophosphate (PIP), PI+SM, PS+PC, PE, and PA. System III consists of hexane/diethylether/formic acid (90:60:12, v/v/v) and separates (also in ascending order): phospholipids (origin), monoglycerides (MG), 1,2-DAG, 1,3-DAG, FFA, TG and cholesterol esters. For systems I and II, which are used to separate the $^{32}$P-labeled phospholipids ($^3$H-inositol radioactivity is used to assess the cross-contamination of lipid classes), between 5000 and 50,000 cpm/sample (depending on experiment) are spotted for analysis. For system III, which is used for DAG analysis, between $5 \times 10^5$ and $1 \times 10^6$ cpm of 3H-AA labeled lipids will be spotted per sample. The lipids are visualized by exposure to iodine vapors and each individual lipid scraped into a scintillation vial. Lipids are extracted from the silica by the addition of 10 ml of Aquassure (New England Nuclear) per tube with vigorous vortexing. Radioactivity is then determined by scintillation counting with correction for quenching.

Phospholipid analysis is performed by comparing cpm of treated CTL to cpm of control, unstimulated CTL. Controls are performed for each timepoint, allowing the data to be presented as change vs control. DAG is calculated as a percent of total lipids and data is presented as the ratio of stimulated CTL to control, unstimulated CTL for each condition and each timepoint.

Analysis of NK Inositol Phosphates

The TCA-diluted samples (stored at $-70°$ C. until analysis) are allowed to thaw without exceeding 4° C. and then mixed by vortex prior to centrifugation for 10 min at 3000 rpm, 4° C. Aqueous supernates, containing $^3$H-myo-inositol and its phosphorylated derivatives (glycerolphosphorylinositol, IP, IP$_2$ and IP$_3$), are separated from the pellets and extracted five times with 2.4 ml of diethylether. Following neutralization to pH 7.0 with 6.25 mM sodium tetraborate, the supernates are applied to anion exchange columns consisting of 1.2 ml of Dowex 1-8 100-200 mesh (formate form, Sigma Chemical Co.) and sequentially eluted as described by Imboden and Stobo *J. Exp.Med.* 161,446 (1985). Inositol and glycerolphosphorylinositol elute together, followed by the sequential elution of IP, P$_2$ and IP$_3$.

Analysis of Protein Phosphorylation

The effects of NK stimulation on de novo protein phosphorylation are analyzed by the following procedure. NK are prepared as described, washed twice in buffer B containing 1 mg/ml BSA and resuspended at $20 \times 10^6$ cells/ml in the same buffer. $^{32}$P-orthophosphate is added to 50-100 µCi/ml and the NK prelabeled for 30-60 min at 37° C. to equilibrate the cellular ATP pools. At the end of this time the NK is processed. For short-term assays (0-30 min), the NK is washed twice and resuspended at $2 \times 10^6$ cells/ml in the buffer. For long-term assays (30 min-24 h), the NK is diluted to $2 \times 10^6$ cells/ml with buffer B without washing and additional radioisotope is added to prevent depletion of the cellular ATP pools. All reactions are initiated by placing the NK at 37° C. Reactions are terminated by the addition of 3 ml of ice-cold PBS containing 10 mM EDTA, 0.1M NaF, 0.1 mM PMSF. The cells are washed twice in such a fashion and the cellular pellets are resuspended in 100 µl of buffer B containing 0.1M NaF, 0.1 mM PMSF, $5 \times 10^{-5}$M 2-mercaptoethanol, 1% Triton X-100. This reaction is incubated for 30 min on ice followed by centrifugation at $2400 \times$ g for 10 min at 4° C. to remove the insoluble nuclear pellet. The supernatant is used as a source of detergent-soluble plasma membrane/cytoplasmic proteins. Proteins associated with the nuclear pellet are extracted by a 30 min treatment on ice with 400 mM NaCl, $5 \times 10^{-5}$M 2-mercaptoethanol, 2 mM MgCl$_2$, 0.1 mM PMSF, 0.1M NaF, 20 mM HEPES, pH 7.5, the pellet again centrifuged and the supernatant collected for analysis.

Two-Dimensional Peptide Mapping.

As described by Accolla *J. Exp.Med.* 157,1053 (1983), the radiolabeled isolated proteins (from the target cell or effector cell immunoprecipitates) are cut out of the dried SDS-PAGE gel and eluted in 0.1% SDS in PBS. The eluted material is reduced with 20 mM dithiothreitol for 60 min, and alkylated with 60 mM iodoacetamide for 30 min. Peptic digestion is performed in 100 µl of formic acid/acetic acid/water 1:4:45 (vol/vol) with pepsin in the presence of bovine serum albumin carrier (1:50 enzyme/protein ratio) for 16 h at 37° C. Two-dimensional peptide mappings is performed on silica gel plates. Electrophoresis is performed in the first dimension, with chromatography performed (at right angles) in the second dimension in n-butanol/acetic acid/water/pryidine 75:15:40:50 (vol/vol).

Selection of Cell Loss Variants

Mutagenesis of the cells (target or effector cells) is performed as described by Kavathas et al *Proc.Natl.Acad.Sci.USA* 77,4251 (1980). $5 \times 10^6$ cells is irradiated with $^{20}$-300 rads, washed and cultured in complete medium at $1 \times 10^6$ cells/ml. After 1 week, the cells are immunoselected by adding a saturating dose of either the anti-target cell or anti-effector cell mAbs and complement. The addition of mAb and complement is repeated every week for a period of 1 month. Cells surviving the immunoselection (cell loss variants) are cloned under limiting dilution conditions, as required.

Modifications and variations of the present invention, a dimeric protein common to the surface of natural killer cells of mammalian and fish origin which functions in recognition of target cells, the antigen on the surface of the cells recognized by the natural kill receptor, mAbs to the receptor and target cell protein, and methods for altering the interaction between natural killer cells and target cells, will be obvious to those skilled in the art from the foregoing detailed description of the invention. Such modifications and variations are intended to come within the scope of the appended claims.

We claim:

1. An antibody to a receptor found as a dimer in the presence of a reducing agent having a subunit with a molecular weight of about 38,000 daltons and a subunit with a molecular weight of about 43,000 daltons, on the surface of natural killer cells of mammalian and fish origin that is recognized by an antibody produced by a hybridoma selected from the group consisting of the hybridomas deposited with ATCC on Oct. 16, 1987 and designated HB9572 and HB9573, wherein the receptor is involved in non-MHC restricted, non-antigen specific cytolysis of target cells.

2. The antibody of claim 1 wherein said receptor recognizes an antigen on the surface of a target cell susceptible of lysis by the natural killer cells.

3. The antibody of claim 2 wherein said antibody is synthesized from a hybridoma produced by fusing a myeloma cell with spleen cells from an animal immunized with fish non-specific cytotoxic cells.

4. The antibody of claim 3 produced by a hybridoma selected from the group consisting of 5C6.10.4, 6D3.2.10, 2B2.4.9, and 6D3.4.4.

5. The antibody of claim 4 produced by a hybridoma deposited with the ATCC as ATCC No. HB9572.

6. The antibody of claim 4 produced by a hybridoma deposited with the ATCC as ATCC No. HB9573.

7. The antibody of claim 1 produced by immunization of an animal with purified antigen isolated by an antigen-antibody technique using a monoclonal antibody derived from a hybridoma produced by fusing a myeloma cell with spleen cells from an animal immunized with fish non-specific cytotoxic cells.

8. An antibody immunoreactive with a target cell antigen present on the surface of cells of mammalian or fish origin susceptible to lysis by natural killer cells, wherein the antigen is a polypeptide having a molecular weight of about 42,000 as determined by SDS gel electrophoresis under either reducing or non-reducing conditions and is immunoreactive with an antibody produced by a hybridoma that was deposited with the ATCC on Oct. 16, 1987 and designated HB9571.

9. The antibody of claim 8 wherein the antigen is recognized by a receptor molecule on the surface of the natural killer cells.

10. The antibody of claim 8 wherein the antibody is derived from a hybridoma produced by fusing a myeloma cell with spleen cells from an animal immunized with a human B lymphoma cell line NC-37.

11. The antibody of claim 10 produced by a hybridoma selected from the group consisting of 18C2.8.3, and 1E7,.

12. The antibody of claim 11 produced by a hybridoma deposited with the ATCC as ATCC No. HB9571.

13. The antibody of claim 11 produced by a hybridoma deposited with the ATCC as ATCC No. HB9574.

14. The antibody of claim 8 produced by immunization of an animal with purified antigen isolated by an antigen-antibody technique using a monoclonal antibody derived from a hybridoma produced by fusing a myeloma cell with spleen cells from an animal immunized with human B lymphoma cell line NC-37.

* * * * *